US009320481B2

(12) United States Patent
Robinson et al.

(10) Patent No.: US 9,320,481 B2
(45) Date of Patent: Apr. 26, 2016

(54) SYSTEMS AND METHODS FOR X-RAY IMAGING

(71) Applicant: GENERAL ELECTRIC COMPANY, Schenectady, NY (US)

(72) Inventors: Vance Scott Robinson, Schenectady, NY (US); Ertugrul Berkcan, Clifton Park, NY (US); Peter Michael Edic, Albany, NY (US); Sergiy Zalyubovsky, Schenectady, NY (US); Marco Francesco Aimi, Schenectady, NY (US); Yizhen Lin, Cohoes, NY (US); Yannan Jin, Schenectady, NY (US); Robert Franklin Senzig, Germantown, WI (US)

(73) Assignee: GENERAL ELECTRIC COMPANY, Niskayuna, NY (US)

( * ) Notice: Subject to any disclaimer, the term of this patent is extended or adjusted under 35 U.S.C. 154(b) by 204 days.

(21) Appl. No.: 14/230,774

(22) Filed: Mar. 31, 2014

(65) Prior Publication Data
US 2015/0272522 A1    Oct. 1, 2015

(51) Int. Cl.
A61B 6/00    (2006.01)
A61B 6/03    (2006.01)

(52) U.S. Cl.
CPC ............... *A61B 6/4035* (2013.01); *A61B 6/035* (2013.01); *A61B 6/482* (2013.01)

(58) Field of Classification Search
CPC ...... A61B 6/482; A61B 6/035; A61B 6/4035; A61B 6/032; G21K 1/10
USPC .......................... 378/4–20, 145, 156, 157, 158
See application file for complete search history.

(56) References Cited

U.S. PATENT DOCUMENTS

| | | | |
|---|---|---|---|
| 6,762,661 B1 | 7/2004 | Higgins | |
| 7,026,602 B2 | 4/2006 | Dausch | |
| 7,826,587 B1 | 11/2010 | Langan et al. | |
| 7,830,216 B1 | 11/2010 | Seth et al. | |
| 8,054,589 B2 | 11/2011 | Gowda et al. | |
| 8,203,319 B2 | 6/2012 | Fujita et al. | |
| 8,311,182 B2 | 11/2012 | Chandra et al. | |
| 8,363,779 B2 | 1/2013 | Chandra et al. | |
| 2010/0283938 A1 | 11/2010 | Chou | |
| 2010/0302691 A1 | 12/2010 | Premerlani et al. | |
| 2010/0331915 A1 | 12/2010 | Hill et al. | |
| 2011/0075810 A1* | 3/2011 | Sendai | A61B 6/4042 378/95 |
| 2011/0127853 A1 | 6/2011 | Fujita et al. | |

(Continued)

FOREIGN PATENT DOCUMENTS

WO    2012007881 A2    1/2012

OTHER PUBLICATIONS

Primak et al., "Dual-source dual-energy CT with additional tin filtration: Dose and image quality evaluation in phantoms and in-vivo", AJR Am J Roentgenol., pp. 1164-1174, vol. 195, Issue 5, Nov. 2010.

(Continued)

*Primary Examiner* — Courtney Thomas
(74) *Attorney, Agent, or Firm* — Fletcher Yoder, P.C.

(57) ABSTRACT

X-ray imaging systems are provided that include an X-ray source and an X-ray detector. A filtering device is positioned between the X-ray source and the X-ray detector and includes one or more micro-filters each adapted to transition between an X-ray filtering position and an X-ray non-filtering position. A controller is programmed to control operation of the micro-filters.

20 Claims, 6 Drawing Sheets

(56) References Cited

U.S. PATENT DOCUMENTS

| | | |
|---|---|---|
| 2012/0031744 A1 | 2/2012 | Naito et al. |
| 2012/0038310 A1 | 2/2012 | Anand et al. |
| 2012/0069952 A1 | 3/2012 | Wu et al. |
| 2012/0076258 A1 | 3/2012 | Chandra et al. |
| 2012/0105944 A1 | 5/2012 | Wang et al. |
| 2012/0169266 A1 | 7/2012 | Anand et al. |
| 2012/0175230 A1 | 7/2012 | Hammond et al. |
| 2012/0193684 A1 | 8/2012 | Sumant et al. |
| 2012/0193685 A1 | 8/2012 | Goldsmith et al. |
| 2012/0314834 A1 | 12/2012 | Yao et al. |

OTHER PUBLICATIONS

Qu et al., "Dual-Energy Dual-Source CT With Additional Spectral Filtration Can Improve the Differentiation of Non-Uric Acid Renal Stones: An Ex Vivo Phantom Study", American journal of roentgenology, pp. 1279-1287, vol. 196, Issue 6, Jun. 2011.

Aulbach., "Dose Neutral Dual Energy Scanning with Dual Source CT", Siemens, Jul. 27, 2011.

* cited by examiner

SYSTEMS AND METHODS FOR X-RAY IMAGING

BACKGROUND

The subject matter disclosed herein relates to multi-energy X-ray imaging systems and, more particularly, to systems and methods for producing increased mean energy separation of X-ray spectra delivered in such systems.

In modern medicine, medical professionals routinely desire to conduct patient imaging examinations to assess the internal condition of a patient in a non-invasive manner. For typical single-energy computed tomography (CT) imaging, the resulting X-ray images are largely a representation of the average density of each analyzed voxel based upon the attenuation of X-rays emitted by the X-ray source by a patient or object, and detected by an X-ray detector. However, for multi-energy X-ray imaging, a greater amount of information may be gleaned for each voxel. For example, in a dual-energy X-ray imaging system, X-rays of two different spectra are applied to the patient or object; high-energy X-ray photons are generally attenuated substantially less by patient tissue than low-energy X-ray photons. In order to reconstruct multi-energy CT projection data, the underlying physical effects of the X-ray interactions with matter, namely, the Compton scattering effects and photoelectric effects, are utilized in a process known as material decomposition (MD), as is known in the art.

During multi-energy CT data acquisition, a multi-energy X-ray source may be used to provide the X-rays having different energy spectra and may be capable of quickly switching between emitting an X-ray spectrum having one average energy to emitting another X-ray spectrum having a different average energy. Such sources are typically called fast-switching kVp (peak operating voltage) sources because the operating voltage to the source is switched quickly between high and low potentials on subsequent CT projection data acquisitions to enable acquisition of projection data closely correlated in both time and space. However, the rapid kVp switching requirements from a single X-ray source limits the ability to employ dynamic beam filtration schemes between the high- and low-energy projection data acquisitions, e.g. rapidly switching a filter out of and into the X-ray beam during low-energy and high-energy acquisitions, respectively. Dynamic filtering schemes are employed to selectively filter the high-energy X-ray spectrum to improve the mean energy separation between the low-energy and high-energy spectra. The mean energy of a spectrum is the energy level of an average photon in the spectrum; it is computed by summing all energies in a given X-ray spectrum after weighting each energy level by the percentage of photons at that specific energy. Thus, without dynamic filtration, there is significant spectral overlap in the low-energy and high-energy projection data acquisitions, limiting the mean energy separation between the two projection data acquisitions. Energy separation is desirable in multi-energy images because it improves the independence of the measurements and enhances the material decomposition process, thereby improving the clinical usefulness of the reconstructed multi-energy images. As known in the art, multi-energy images comprise basis material images, monochromatic images (images reconstructed as if the applied X-ray spectrum consisted of a single energy), or images reconstructed directly from an applied energy spectrum. Accordingly, there exists a need for systems that enable multi-energy X-ray imaging with a fast-switching kVp source and dynamic filtering schemes in order to increase the mean energy separation of the applied X-ray spectra.

BRIEF DESCRIPTION

In one embodiment, a multi-energy X-ray imaging system is provided. In accordance with this embodiment, the multi-energy X-ray imaging system includes an X-ray source configured to emit X-rays toward an imaging volume and an X-ray detector configured to produce an electrical signal corresponding to the intensity of the X-rays that reach the X-ray detector after passing through the imaging volume. The multi-energy X-ray imaging system also includes a filtering device comprising an array of micro-filters each configured to transition between an X-ray filtering position and an X-ray non-filtering position, and being positioned between the X-ray source and the X-ray detector. The multi-energy X-ray imaging system additionally includes a controller programmed to acquire a first set of projection data when applying a first energy spectrum by controlling the X-ray source to emit the X-rays with the first energy spectrum and controlling one or more of the micro-filters to be in the non-filtering position. The controller is further programmed to acquire a second set of projection data when applying a second energy spectrum with a mean energy greater than the mean energy of the first energy spectrum by controlling the X-ray source to emit the X-rays at the second energy spectrum and controlling one or more of the micro-filters to be in the filtering position.

In an additional embodiment, an X-ray imaging system is provided. In accordance with this embodiment, the X-ray imaging system includes an X-ray source configured to emit X-rays toward an imaging volume and an X-ray detector configured to produce an electrical signal corresponding to the intensity of the X-rays that reach the X-ray detector after traveling through the imaging volume. The X-ray imaging system also includes a filtering device positioned between the X-ray source and the X-ray detector. The filtering device includes one or more micro-filters each configured to transition between an X-ray filtering position and an X-ray non-filtering position. The X-ray imaging system additionally includes a controller programmed to acquire a set of projection data when controlling the one or more micro-filters to be in either a non-filtering position or a non-filtering position so as to modulate one or more of the X-ray flux or spectral characteristics within the imaging volume or at the detector.

In a further embodiment, a multi-energy X-ray imaging method is provided. In accordance with this method, steps are performed including: controlling an X-ray source to emit X-rays with a first energy spectrum; controlling one or more of micro-filters, positioned between the X-ray source and an X-ray detector, to be in an X-ray non-filtering position when the X-ray source emits the X-rays with the first energy spectrum; controlling the X-ray source to emit the X-rays with a second energy spectrum with a mean energy greater than the mean energy of the first energy spectrum; and controlling the one or more micro-filters to be in an X-ray filtering position when the X-ray source emits the X-rays with the second energy spectrum.

In another embodiment, an X-ray imaging method is provided. In accordance with this method, steps are performed including: controlling an X-ray source to emit X-rays; controlling one or more of micro-filters, positioned between the X-ray source and an X-ray detector, each configured to transition between an X-ray filtering position and an X-ray non-filtering position, so as to modulate one or more of the X-ray flux or spectral characteristics within the imaging volume or at the detector; and controlling acquisition of projection data by the X-ray detector when the one or more micro-filters are configured in either the X-ray filtering position or the X-ray non-filtering position.

BRIEF DESCRIPTION OF THE DRAWINGS

These and other features, aspects, and advantages of the present invention will become better understood when the following detailed description is read with reference to the accompanying drawings in which like characters represent like parts throughout the drawings, wherein.

DETAILED DESCRIPTION

Figure 1:
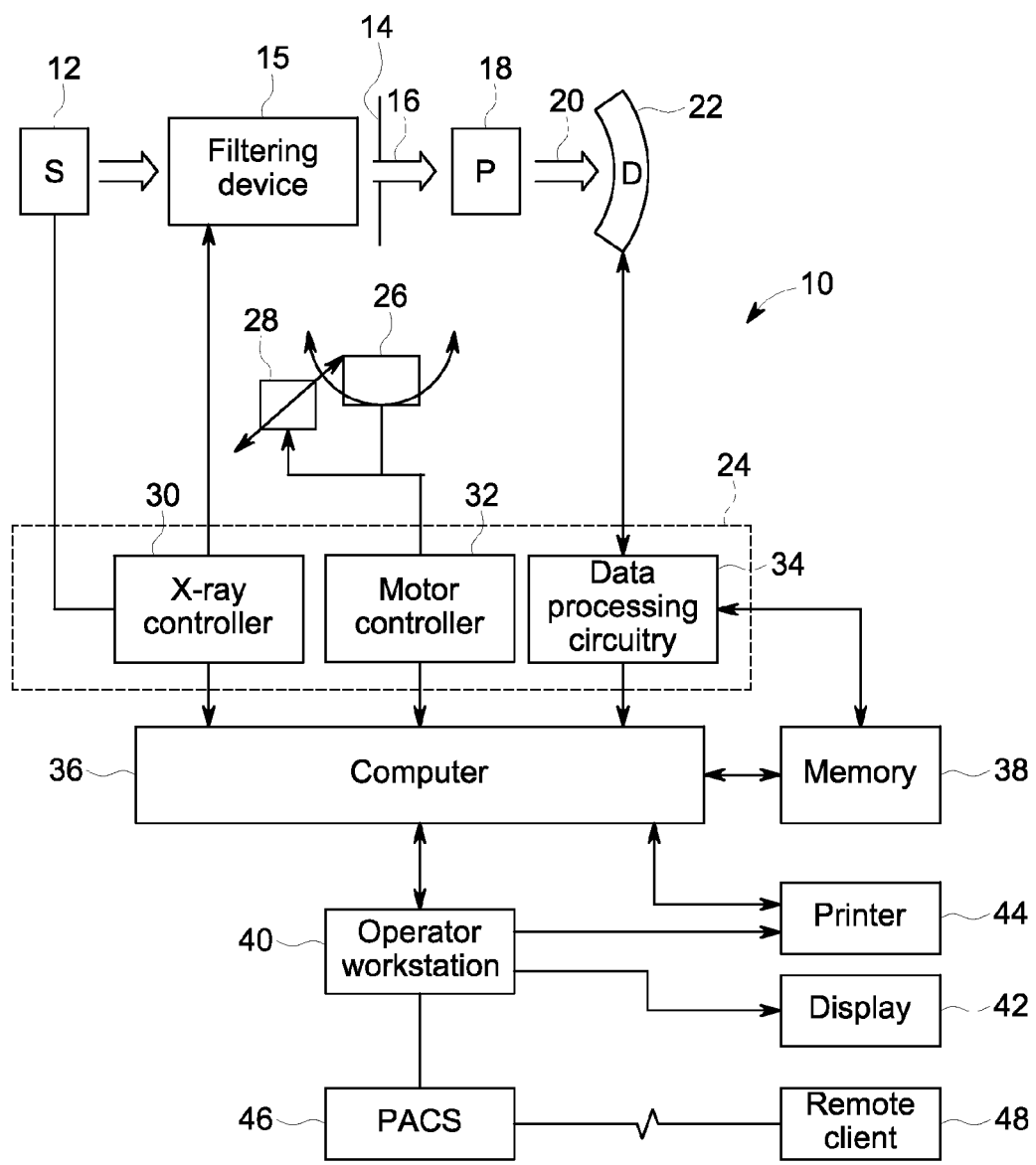
FIG. 1 illustrates an embodiment of a multi-energy CT imaging system, in accordance with aspects of the present disclosure.

The disclosed embodiments are directed to multi-energy X-ray systems and methods that enable increased mean energy separation between applied energy spectra. For example, one embodiment enables greater mean energy separation between applied high- and low-energy X-ray spectra in dual-energy computed tomography (CT) imaging. In dual-energy CT operations, the same section of a patient or object is imaged using two different energy spectra, e.g., a spectrum generated with the operating voltage of the X-ray tube selected to be 80 kVp and 140 kVp for the low-energy and high-energy projection data acquisitions, respectively; projection data are acquired from a single point of reference of the X-ray tube and detector relative to the section of the patient or object being scanned. Although scanning of a patient will be mentioned exclusively hereafter, these techniques equally apply to scanning inanimate objects. By considering the complimentary projection data that are measured and making assumptions about the materials likely present within the patient (i.e., bone, iodine, water, fat, tissue, etc. for human CT scanning), the different materials within the field of view may be identified. The presently enabled greater mean energy separation between the X-ray spectra from the 2 complimentary low- and high-energy exposures may allow an operator to obtain resulting multi-energy images with improved material decomposition fidelity for clinical evaluation.

In one embodiment, the increased mean energy separation is achieved by positioning an array of micro-filters between an X-ray source and an imaged subject. Since X-ray filtering may be desired during acquisition of the high-energy projection data but not during acquisition of the low-energy projection data, it is therefore desirable for the filtering material to be moved in and out of, respectively, the X-ray path quickly (e.g., in less than approximately 10 microseconds) as the multi-energy X-ray tube switches the operating voltage of the X-ray tube to acquire the high- and low-energy projection data acquisitions. The embodiments described herein provide mechanisms that enable quick switching speeds by discretizing needed filtering material into an array of micro-filters, thus incrementally decreasing the mass and motion required of each filtering element, thereby reducing the inertia forces that would otherwise limit the desired switching speeds.

In some provided embodiments, the array of micro-filters transition between an X-ray filtering position and an X-ray non-filtering position during projection data acquisition. When in the X-ray filtering position, the micro-filter array functions as a high-pass spectral filter, attenuating a portion of the low-energy X-ray flux within the spectrum. That is, when in the X-ray filtering position, the micro-filter array attenuates low-energy X-rays from passing through the array toward the subject (i.e., the patient or object to be imaged). On the other hand, when the micro-filter array is positioned in the X-ray non-filtering position, the profile of micro-filter array is reduced such that it blocks a minimal percentage of the X-ray flux emitted by the X-ray source toward the patient. For example, in some embodiments, although the micro-filter array is positioned in the X-ray non-filtering position, portions of the array may still effectively block some emitted X-rays from the source, thus preventing a minimal number of X-rays from reaching the patient.

With the forgoing discussion in mind, FIG. 1 illustrates diagrammatically an imaging system 10 for acquiring and processing projection data. In the illustrated embodiment, system 10 is a multi-energy computed tomography (CT) system designed to acquire multi-energy and non-multi-energy X-ray projection data, to reconstruct the projection data into an image, and to process the image data for display and analysis in accordance with the present techniques. Though the imaging system 10 is discussed in the context of medical imaging, the techniques and configurations discussed herein are applicable in other non-invasive imaging contexts, such as baggage, part, or package screening. In the embodiment illustrated in FIG. 1, multi-energy CT imaging system 10 includes a source 12 of X-ray radiation. As discussed in detail herein, the source 12 of X-ray radiation is a multi-energy X-ray source, such as an X-ray tube, or a distributed X-ray source configured to emit X-rays from different locations along a surface. For example, the multi-energy X-ray source 12 may include one or more addressable solid-state electron emitters. Such solid-state electron emitters may be configured as arrays of field emitters, including one-dimensional arrays, i.e., lines, and two-dimensional arrays. The multi-energy X-ray source is configured to emit X-rays of two or more energy spectra. For example, a multi-energy X-ray source 12 may be capable of emitting X-rays of 2, 3, 4, 5, or more different energy spectra upon application of 2, 3, 4, 5, or more different operating voltages.

The multi-energy X-ray source 12 may be positioned proximate to a collimator 14. The collimator 14 may consist of one or more collimating regions, such as lead or tungsten shutters, for each emission point of the source 12. The collimator 14 typically defines the size and shape of the one or more beams of radiation 16 that pass into a scanning volume in which a subject, such as a human patient 18, is positioned. A beam of radiation 16 may be generally fan-shaped or cone-shaped, depending on the configuration of the detector array.

An unattenuated portion of the radiation 20 passes through the subject, which attenuates the one or more beams of radiation 16, and impacts a detector array, represented generally at reference numeral 22.

The detector 22 is generally formed by a plurality of detector elements, which detect the X-rays that pass through and around a subject of interest. Each detector element produces an electrical signal that represents the intensity of the X-ray beam incident at the position of the element during a data acquisition interval when the beam strikes the detector. Typically, signals are acquired at a variety of angular positions of the X-ray source 12 and detector 22 relative to the subject of interest so that a plurality of projection views may be collected. These signals are acquired and processed to reconstruct one or more images of the features within the subject, as described below.

Further, a filtering device 15 is positioned between the X-ray source 12 and the collimator 14. However, in other embodiments, the filtering device 15 may be positioned in any implementation-specific position between the X-ray source 12 and the detector 22. As discussed in more detail below, the filtering device 15 may include an array of micro-filters (or multiple arrays of micro-filters) that are controllable to be physically positioned and repositioned such that the array of micro-filters substantially filter the X-ray beam 16 along paths connecting X-ray source 12 to individual detector cells of detector array 22 (X-ray filtering position) or repositioned to minimally obstruct the X-ray beam before the X-rays reach the patient 18 (X-ray non-filtering position). By discretizing the filtering device 15 into an array of micro-filters, presently disclosed embodiments enable the elements of the filtering device 15 to be physically repositioned in a time period that meets a desired switching requirement (e.g., in less than 10 microseconds, less than 20 microseconds, etc.).

This feature may be advantageous because in multi-energy X-ray systems, it is desirable for the X-ray source 12 to rapidly switch between high and low peak operating voltages to enable acquisition of closely correlated projection data—both in space and time—using the chosen X-ray energy spectra. Discretization of the filtering device 15 into the micro-filter array enables the mass of the filtering device 15 to be broken up into smaller components, thus enabling the physical repositioning of the elements of the filtering device 15 to accommodate the rapid speed at which the X-ray source switches between the high- and low-energy X-ray spectra. That is, when considering a conventional dual-energy X-ray imaging system, the rapid switching of the operating tube voltage when using a single X-ray source 12 limits the ability to change X-ray beam filtration by sequentially inserting and removing the filter from the X-ray beam 16 between projection data acquisitions; such a feature is enabled by presently disclosed systems.

The multi-energy X-ray source 12 is controlled by a system controller 24, which furnishes power, focal spot location, control signals and so forth for CT examination sequences. Moreover, the detector 22 is coupled to the system controller 24, which commands acquisition of the signals generated in the detector 22. The system controller 24 may also execute various signal processing and filtration functions, such as for initial adjustment of dynamic ranges, interleaving of digital projection and/or image data, and so forth. In general, system controller 24 commands operation of the imaging system to execute examination protocols and to process acquired data. In the present context, system controller 24 also includes signal processing circuitry and associated memory circuitry. The associated memory circuitry may store programs and routines executed by the system controller, configuration parameters, projection and/or image data, and so forth. In one embodiment, the system controller 24 may be implemented as all or part of a processor-based system such as a general purpose or application-specific computer system.

In the embodiment illustrated in FIG. 1, system controller 24 may control the movement of the elements of the filtering device 15, as well as a linear positioning subsystem 28 and rotational subsystem 26 via a motor controller 32. In imaging system 10 in which the source 12 and/or the detector 22 may be rotated, the rotational subsystem 26 may rotate the X-ray source 12, the collimator 14, the filtering device 15, and/or the detector 22 through one or multiple turns around the patient 18. It should be noted that the rotational subsystem 26 may include a gantry. The linear positioning subsystem 28 enables the patient 18, or more specifically a patient table, to be displaced linearly through a gantry to facilitate imaging procedures. Thus, the patient table may be linearly moved within the gantry or within the imaging volume defined by the source 12 and/or detector 22 configuration to generate images of particular areas of the patient 18. In embodiments having a stationary source 12 and a stationary detector 22, the rotational subsystem 26 may be absent. Similarly, in embodiments in which the source 12 and the detector 22 are configured to provide extended or sufficient coverage along the Z-axis, i.e, the axis associated with the main length of the patient 18, the linear positioning subsystem 28 may be absent.

Further, the system controller 24 may include data processing circuitry 34. In this embodiment, the detector 22 is coupled to the system controller 24, and more particularly to the data processing circuitry 34. The data processing circuitry 34 receives data collected by the detector 22. The data processing circuitry 34 typically receives sampled analog signals from the detector 22 and converts the data to digital signals for subsequent processing by a processor-based system, such as a computer 36. Alternatively, in other embodiments, the detector 22 may include a digital-to-analog converter to convert the sampled analog signals to digital signals prior to transmission to the data processing circuitry 34. Additionally, in certain embodiments, the data processing circuitry 34 that may be selectively activated by the system controller 24 (e.g., via activation signals) to receive signals from the detector 22.

Additionally, the multi-energy X-ray source 12 and/or the filtering device 15 may be controlled by an X-ray controller 30 disposed within the system controller 24. The X-ray controller 30 may be configured to provide power and timing signals to the X-ray source 12 and/or the filtering device 15. For example, the X-ray controller 30 may include a fast-switching kVp power supply configured to supply the source 12 with at least two or more operating voltage levels to produce X-rays of two or more energy spectra. The X-ray controller 30 may coordinate the switching of the power supply providing power to source 12 with the physical repositioning of the elements of the filtering device 15. Additionally, in some embodiments, the X-ray controller 30 may include sensing and processing circuitry configured to monitor the position of the elements in the filtering device 15.

In certain embodiments, the system controller 24 may include a synchronizing signal such as a clock (e.g., a signal generated from a time processing unit) such that the activities of the components of the CT imaging system 10 may be synchronized. For example, the clock may provide signals to enable the system controller 24 to correlate in time the application of a lower or higher operating voltage level to the X-ray source 12 with the transitioning of the filtering device 15 between the X-ray filtering position and the X-ray non-filtering position.

In the depicted embodiment, the computer 36 is coupled to the system controller 24. The data collected by the data processing circuitry 34 may be transmitted to the computer 36 for subsequent processing and reconstruction. The computer 36 may include or communicate with a memory 38 that can store data processed by the computer 36, data to be processed by the computer 36, or routines to be executed by the computer 36, such as for processing projection data in accordance with the present technique. It should be understood that any type of computer accessible memory device capable of storing the desired amount of data and/or code may be utilized by such a system 10. Moreover, the memory 38 may comprise one or more memory devices, such as magnetic or optical devices, of similar or different types, which may be local and/or remote to the system 10. The memory 38 may store data, processing parameters, and/or computer programs having one or more routines for performing the processes described herein.

The computer 36 may also be adapted to control features enabled by the system controller 24, i.e., scanning operations and data acquisition. Furthermore, the computer 36 may be configured to receive commands and scanning parameters from an operator via an operator workstation 40 which may be equipped with a keyboard and/or other input devices. An operator may thereby control the system 10 via the operator workstation 40. Thus, the operator may observe one or more reconstructed images and other data relevant to the system from computer 36, initiate imaging sequences, select and apply image filters, and so forth. Further, the operator may manually identify features and regions of interest from the reconstructed images or the operator may review features and regions of interest automatically identified and/or enhanced through computer-aided geometry determination as discussed herein. Alternatively, automated detection algorithms may be applied to such enhanced features or regions of interest.

A display 42 coupled to the operator workstation 40 may be utilized to observe the reconstructed images. Additionally, the reconstructed images may be printed by a printer 44 which may be coupled to the operator workstation 40. The display 42 and printer 44 may also be connected to the computer 36, either directly or via the operator workstation 40. Further, the operator workstation 40 may also be coupled to a picture archiving and communications system (PACS) 46. It should be noted that PACS 46 might be coupled to a remote system 48, radiology department information system (RIS), hospital information system (HIS) or to an internal or external network, so that others at different locations may gain access to the image data.

One or more operator workstations 40 may be linked in the system for outputting system parameters, requesting examinations, viewing images, and so forth. In general, displays, printers, workstations, and similar devices supplied within the system may be local to the data acquisition components, or may be remote from these components, such as elsewhere within an institution or hospital, or in an entirely different location, linked to the image acquisition system via one or more configurable networks, such as the Internet, virtual private networks, and so forth.

Figure 2A:
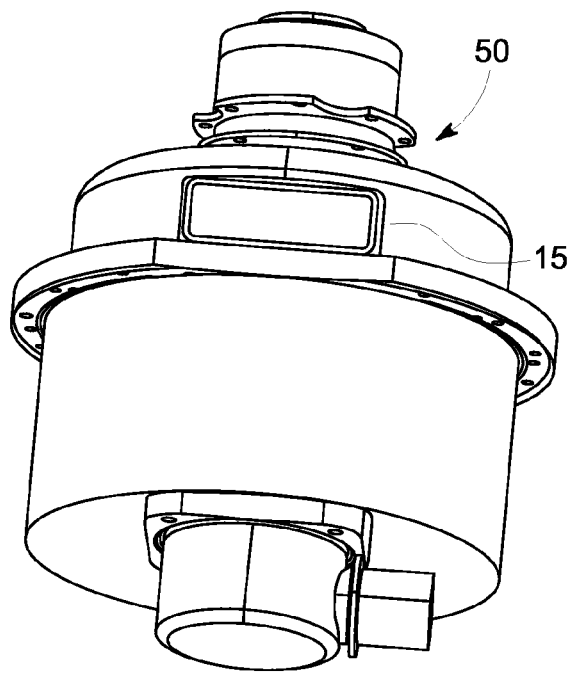
FIG. 2A is a perspective view of an embodiment of a multi-energy X-ray imaging tube in accordance with an embodiment.
Figure 2B:
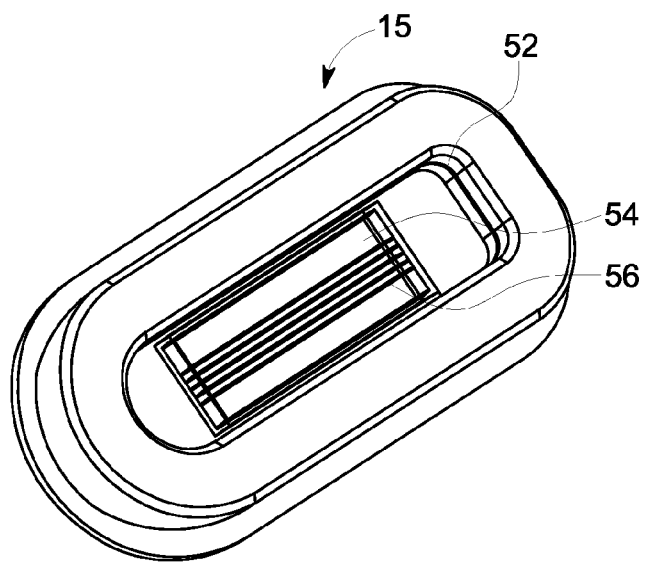
FIG. 2B is a perspective view of an embodiment of a filtering device disposed in or adjacent to the imaging tube of FIG. 2A.
Figure 2C:
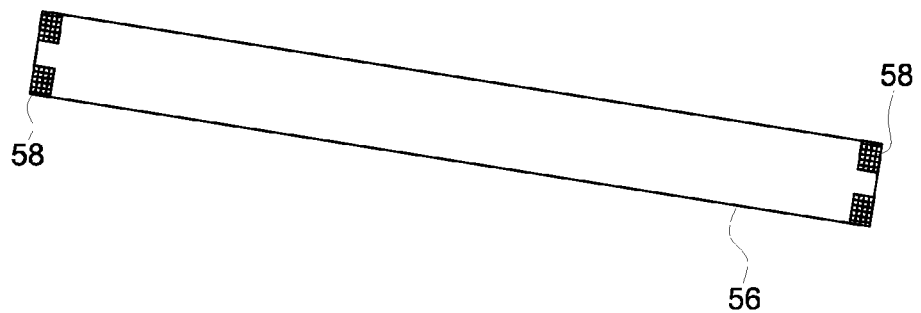
FIG. 2C is a perspective view of an embodiment of a panel disposed in the filtering device of FIG. 2B.

FIGS. 2A-C illustrate one possible placement and configuration of the filtering device 15 in accordance with an embodiment. Particularly, FIG. 2A illustrates an X-ray tube 50 having the filtering device 15 disposed therein. The filtering device 15 is positioned within the tube 50 such that the X-rays pass through the filtering device 15 after being generated within the tube 50. In alternate embodiments, the filtering device 15 may be external to the X-ray tube. In either embodiment, the filtering device 15 may be provided as a package having a housing 52, as shown in FIG. 2B. In some embodiments, the housing 52 may be a hermetic enclosure that isolates the interior components from the surrounding environment and allows for the filtering device to operate in different gaseous environments and/or at reduced vacuum. In certain embodiments, different gaseous species may allow higher applied actuation voltages. Further, in some embodiments, reduced ambient pressure may reduce the drag experienced by the paddles as they rotate. The filtering device 15 also includes a support structure 54 that supports a plurality of panels 56. Although five panels 56 are shown for illustrative purposes, any desired number of panels may be included in other embodiments, depending on implementation-specific considerations. For example, in one dual-energy CT embodiment, the filter's location with respect to the focal spot and the distance from the focal spot to the detector determines the cross-sectional area of the X-ray beam emitting from the source to be 10-20 mm in height. If each panel of micro-filters deflects to filter 100 um of the 10-20 mm X-ray beam height, approximately 100-200 panels are needed to completely filter the X-ray beam. FIG. 2C illustrates the panel 56 in more detail. Each panel 56 may support one or more arrays of micro-filters 58. In the illustrated embodiment, the micro-filter arrays are formed as micro-electromechanical system (MEMS) arrays. Further, in FIG. 2C, only four micro-filters arrays 58 are shown for illustrative purposes, but in some embodiments, the panel may be covered in micro-filters arrays 58.

Figure 3A:
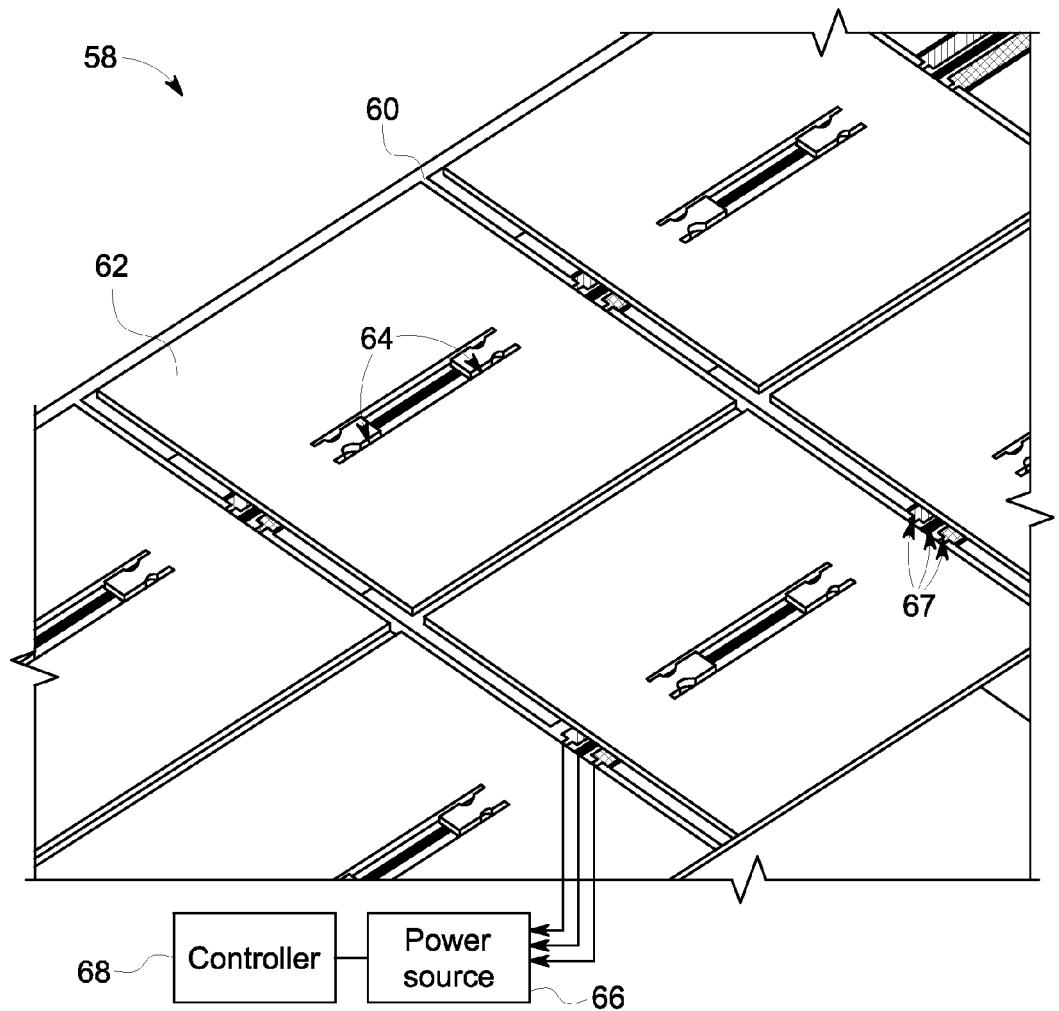
FIG. 3A illustrates an embodiment of a micro-filter array disposed in an X-ray non-filtering position in accordance with an embodiment.
Figure 3B:
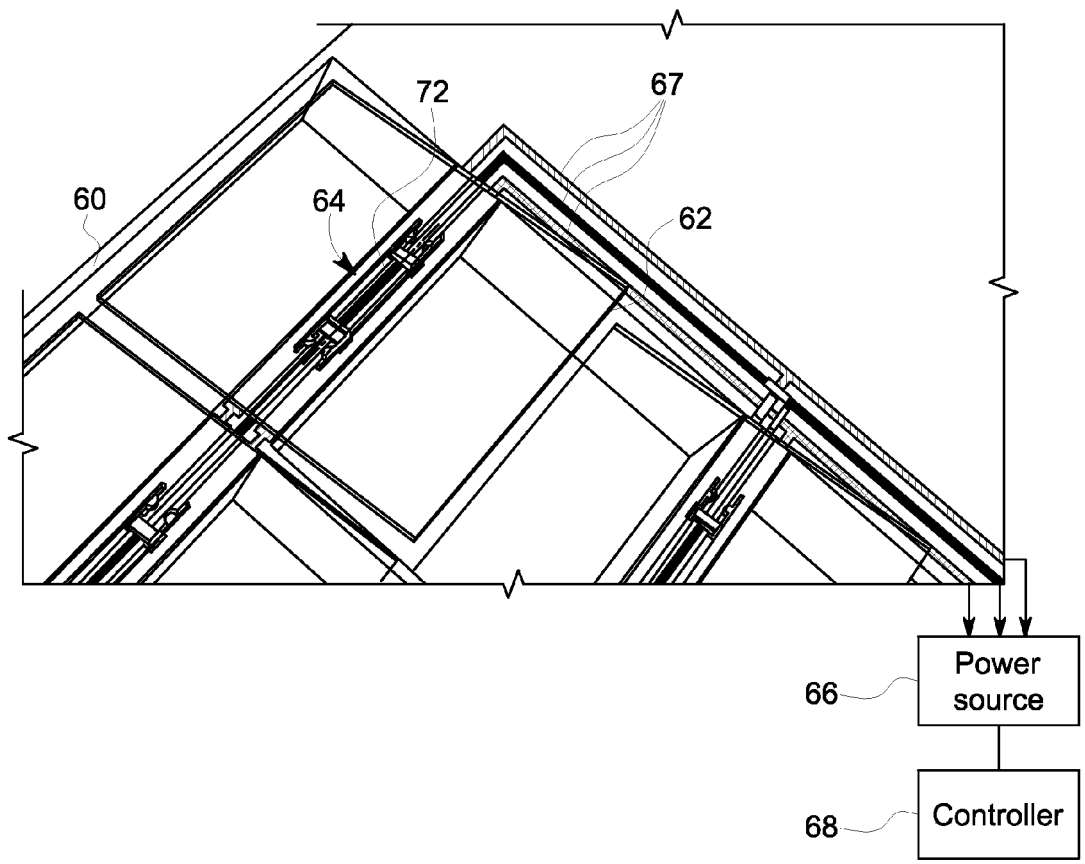
FIG. 3B illustrates an embodiment of a micro-filter array disposed in an X-ray filtering position in accordance with an embodiment.
Figure 3C:
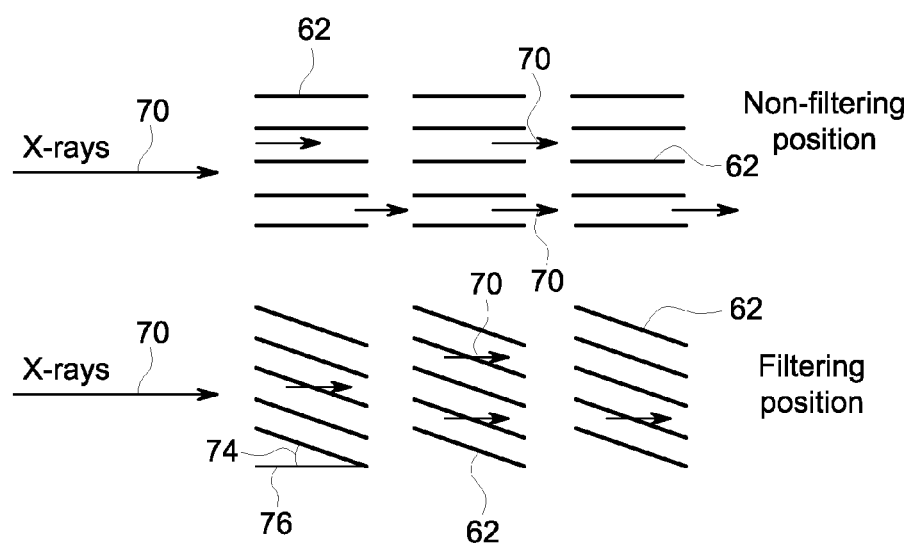
FIG. 3C is a schematic illustrating operation of the micro-filter array illustrated in FIGS. 3A and 3B in accordance with an embodiment.

FIG. 3A illustrates a portion of an embodiment of the micro-filter array 58 in which the elements of the micro-filter array 58 are disposed in the X-ray non-filtering position. FIG. 3B illustrates a portion of an embodiment of the micro-filter array 58 in which the elements of the micro-filter array 58 are slightly tilted and disposed in the X-ray filtering position. The micro-filter array 58 includes a support structure 60 having a plurality of paddles 62 coupled thereto via torsional spring structure 64. Each paddle 62 is electrically connected to a power source 66 under control of a controller 68 via electrical connections 67. Referring in FIG. 1, controller 68 may be part of system controller 24, or more specifically, X-ray controller 30. FIG. 3C is a schematic illustrating the positioning of the paddles 62 in the filtering and non-filtering positions with respect to X-rays 70 emitted by an X-ray source.

During operation, the controller 68 determines an appropriate voltage level for the panel 56 and activates the power source 66 to output the power needed to electrostatically actuate the paddles 62 and move them into the desired position. For example, if the controller 68 determines that the paddles 62 should be transitioned between the current position and the opposing position (e.g., between the high- and low-energy projection data acquisitions), a voltage that attracts the paddles 62 to the desired position is applied to the panel 56. Upon application of the voltage, the paddles 62 each pivot about a fixed midpoint disposed on central axis 72 to implement either the X-ray non-filtering position shown in FIG. 3A or the X-ray filtering position shown in FIG. 3B. In practice, this may be accomplished by providing an individual electrode associated with each paddle (thus allowing separate and independent actuation of each respective paddle) or by providing larger electrodes that each span multiple paddles (i.e., separate subsets of paddles), thereby allowing separate actuation of each spanned subset of paddles relative to the whole. Although an electrostatic actuation method is explicitly described, magnetic and thermal actuation schemes are also envisioned.

That is, to transition the paddles 62 between the X-ray filtering and non-filtering positions, an angle 74 of the paddles 62 with respect to an upper surface 76 of support structure 60 is altered. For example, as shown in FIG. 3C, the paddles 62 may be flat with respect to upper surface 76 when positioned in the non-filtering position. As shown, when the X-rays 70 approach the paddles 62, the X-rays are allowed to pass between the paddles 62 toward the patient. It should be noted, however, that some of the X-rays 70 may impinge on the sides of paddles 62, giving rise to minimal filtering. In some embodiments, when the paddles 62 are positioned in the non-filtering position, greater than approximately 75% of the X-rays 70 may pass between the paddles 62 toward the patient.

However, when the paddles 62 are positioned in the filtering position, the angle 74 is varied such that the X-rays 70 from the X-ray source pass through the paddles 62 and are thus filtered before reaching the patient. In some embodiments, the angle 74 may be varied depending on implementation-specific considerations. For example, in one dual-energy CT embodiment, the angle 74 may be approximately 25 degrees. Further, in some embodiments, the paddles 62 may include an X-ray filtering material to facilitate the blocking or filtering of the X-rays 70 when the paddles 62 are positioned in the X-ray filtering position. By varying the angle of the paddle one can control the thickness of material that the X-rays pass through.

Portions of the micro-filter array may be formed from a variety of suitable materials. For example, the paddles 62 may include a material having a k-edge below the mean energy of the high-energy X-ray spectrum. For further example, in one embodiment, the support structure 60 may be formed from silicon, and the paddles 62 may be formed from tin. In another embodiment, the paddles 62 may be formed from tin, and the support structure 60 may be formed from silicon dioxide.

It should be noted that although the filtering device 15 is described herein for use with dual-energy CT imaging applications, the filtering device 15 may be used in a variety of other suitable implementations as well. For example, the filtering device 15 may be used in region-of-interest imaging in one of standard CT imaging applications, dual-energy CT imaging applications, or multi-energy CT applications, where only the X-rays directed towards one or more regions of interest are allowed to pass and the others are attenuated by the filtering device. Since the paddles 62 are individually addressable, the amount of flux that passes through the filtering device 15 may be controlled in a pixelated fashion in some embodiments. While for dual-energy imaging, it may be desirable to control the paddles 62 between two positions, filtering and non-filtering, in certain region-of-interest imaging embodiments, the paddles 62 may be controlled between a non-filtering position and a filtering position, which may selectively filter the X-ray beam or substantially block the X-ray beam. When the paddles are in the filtering position which substantially blocks the X-ray beam, portions of the beam that are outside one or more regions of interest to be imaged are substantially blocked, for example, by controlling the number of actuated panels 56 and/or devices within that panel 56.

Further, in some embodiments, the filtering device 15 may be utilized to modify the spectral characteristics of the X-ray beam incident on the imaging volume and/or control the flux uniformity at the detector in one of standard CT imaging applications, dual-energy CT imaging applications, or multi-energy CT applications. In one example, the filtering device 15 may be used to selectively filter the X-ray beam in the transverse and longitudinal directions so as to make the spectral characteristics of the X-ray beam more uniform within the imaging volume. Also, the filtering device may be used to selectively remove low-energy components so as to reduce patient dose. In another example, the filtering device 15 may be utilized for minimizing the dynamic range required by the detector by varying the attenuation across the field of view based on the anticipated attenuation by the object being imaged so that the flux at the detector has better uniformity. For a further example, for imaging of a patient's abdomen, a specially-shaped filter that is thick at the ends of the fan beam and narrow in the middle of the fan beam would allow a flux profile incident on the abdomen that was more intense in the middle than at the edges. If chosen appropriately, the intensity profile incident on the detector after passing through the oval shaped abdomen would be fairly uniform. With the pixelated filtering device 15 described herein, in accordance with certain embodiments, the attenuation may be adaptively changed throughout the imaging sequence as the gantry comprising the X-ray source and detector rotates around the patient to ensure a more uniform flux profile at the detector for all projection data acquisitions. In these embodiments, the dose efficiency of the CT system may be improved because the system only provides the amount of flux through the filter as necessary for the imaging application. The foregoing features may be applicable, for example, in systems including a photon counting detector to reduce detector performance requirements, e.g., maximum count rate requirement, and mitigate detector pile-up concerns.

Further, in some embodiments in one of standard CT imaging applications, dual-energy CT imaging applications, or multi-energy CT applications, the filtering device 15 may be positioned adjacent to the detector 22 and utilized to block a portion of the active area of one or more individual detector cells comprising detector 22, commonly denoted as a "comb" filter. This system and method is useful for selectively enhancing the resolution capability of the CT imaging system since the effective area of the detector cells is reduced, which enhances the resolution in reconstructed images. Furthermore, a filtering device 15 may be used to selectively filter a subset of the detector cells comprising detector 22 in this manner, to provide adaptive high-resolution imaging capability within one or more regions of interest within the patient. This method is useful for high-resolution imaging of selective areas of the patient, such as in the coronary arteries of the heart or portions of the inner ear.

As described above, system concepts and methods to selectively shape or modulate the X-ray flux intensity and/or spectral characteristics within the imaging volume or at the detector are useful for standard CT imaging applications, dual-energy CT imaging applications, or multi-energy CT applications. Although not limiting, certain embodiments include one of confining the X-ray flux to illuminate one or more identified regions of interest within the imaging volume, adaptively controlling the X-ray flux incident on the detector so that it is more uniform with regards to spectral characteristics and/or intensity, and blocking a portion of the active area of a plurality of individual detector cells for selective resolution enhancement within one or more regions of interest within the imaging volume.

Figure 4:
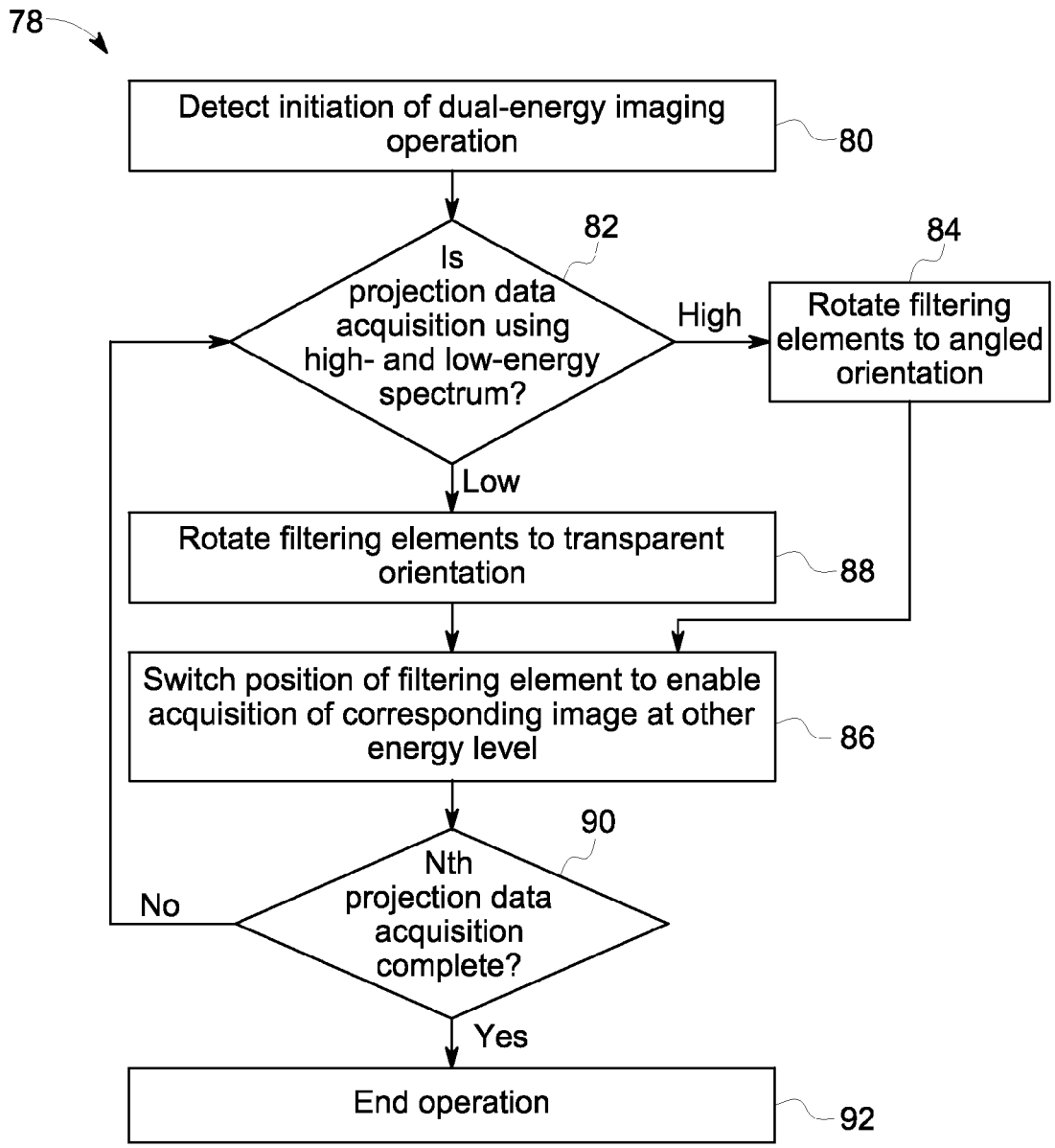
FIG. 4 is a flow chart illustrating an embodiment of a method for acquiring dual-energy projection data with increased energy separation in accordance with an embodiment.

FIG. 4 illustrates an embodiment of a method 78 that may be implemented by a controller to appropriately position the filtering elements (e.g., paddles 62) for use in a dual-energy X-ray or CT imaging operation. The method 78 begins with detection of the initiation of the imaging operation (block 80). The method 78 proceeds with an inquiry as to whether the projection data acquisition corresponds to application of a high- or low-energy X-ray spectrum (block 82). If the projection data being acquired corresponds to the high-energy X-ray spectrum, the controller controls the filtering elements to rotate to an angled orientation to position the filtering elements in the filtering position (block 84). Once projection data are acquired for the high-energy X-ray spectrum, the position of the filtering elements is switched to enable acquisition of the corresponding projection data when applying the low-energy spectrum (block 86). Conversely, if the initial projection data are being acquired when applying the low-energy X-ray spectrum, the filtering elements are first rotated to the substantially-transparent or non-filtering position (block 88) before being rotated to the filtering position to acquire the corresponding projection data when applying the high-energy X-ray spectrum (block 86).

After each set of corresponding projection data are obtained in this manner, the method 78 includes an inquiry as to whether the last desired projection data pair (projection data acquired when sequentially applying the high- and low-energy spectrum, or vice versa) has been acquired (block 90), and the operation is ended when all the desired projection data pairs have been acquired (block 92). It should be noted that the filtering elements may be switched between the filtering and non-filtering orientations in less than 10 microseconds due to the discretization of the filtering device 15 into the micro-filter arrays. The corresponding quick switching speed enables the filtering elements to be transitioned between the two positions quickly enough to accommodate the pace of the fast-switching kVp X-ray source.

Figure 5:
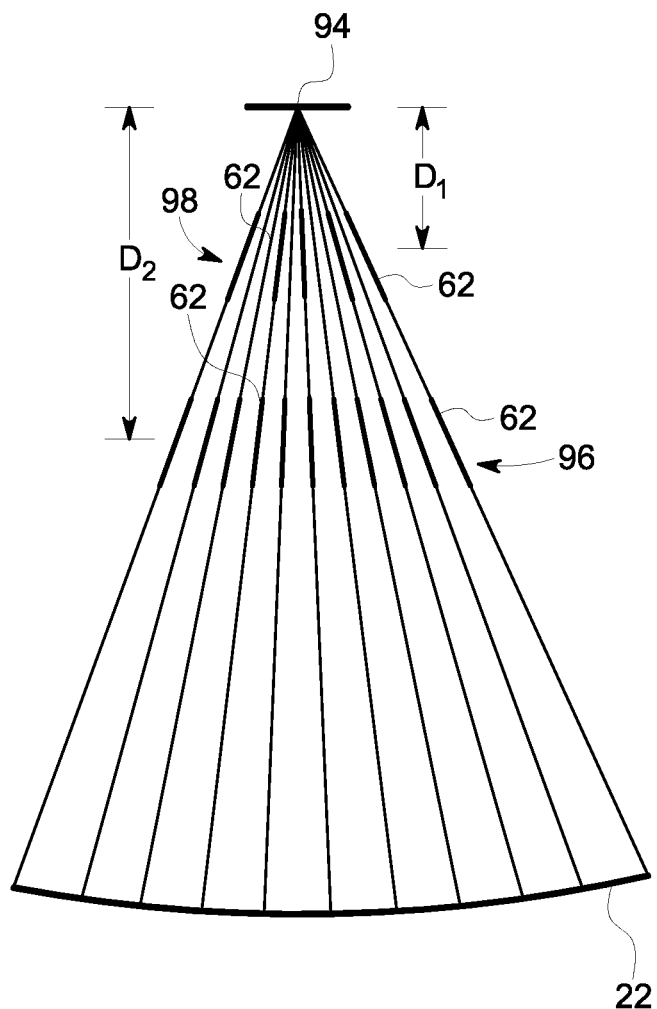
FIG. 5 is a schematic illustrating alignment of the elements of the micro-filter array with the X-ray beam emitted from the focal spot of the X-ray source in accordance with an embodiment.

It should be noted that a variety of parameters of the micro-filter arrays disclosed herein may be tuned depending on implementation-specific considerations. For example, the thickness of the paddles may be altered along with the switching angle of the paddles. For further example, the number of paddles may be increased or decreased in certain embodiments. FIG. 5 is a schematic illustrating how the number of paddles may be chosen in accordance with one embodiment.

As illustrated, the distance at which the paddles 62 are located from a focal spot 94 of the X-ray source 12 may impact the quantity of paddles included in a given system. For example, if the paddles 62 are positioned at the first distance ($D_1$), for example, 80 mm, from the focal spot 94, fewer paddles 62 are required than if the paddles 62 are positioned further from the focal spot 94 at the second distance ($D_2$), for example, 160 mm. Further, it should be noted that in some embodiments, the angle of each of the paddles 62 in a given row of paddles, for example, either row 96 or row 98, may be altered based on its location with respect to the location of the focal spot. The foregoing feature may enable alignment of each paddle with the X-ray beam emitted from the focal spot 94 of the X-ray source to maintain focal alignment in the system.

This written description uses examples to disclose the invention, including the best mode, and also to enable any person skilled in the art to practice the invention, including making and using any devices or systems and performing any incorporated methods. The patentable scope of the invention is defined by the claims, and may include other examples that occur to those skilled in the art. Such other examples are intended to be within the scope of the claims if they have structural elements that do not differ from the literal language of the claims, or if they include equivalent structural elements with insubstantial differences from the literal languages of the claims. For example, although discussed above with reference to CT imaging, the techniques described herein are equally applicable to X-ray projection imaging, where only a limited number of orientations of the X-ray source and detector relative to the patient are required. Additionally, the orientation of the panels 56 may be aligned with one of the cone- and fan-angle of the X-ray beam emitted from X-ray source 12.

The invention claimed is:

1. A multi-energy X-ray imaging system, comprising:
   an X-ray source configured to emit X-rays toward an imaging volume;
   an X-ray detector configured to produce an electrical signal corresponding to the intensity of the X-rays that reach the X-ray detector after passing through the imaging volume;
   a filtering device comprising an array of micro-filters each configured to transition between an X-ray filtering position and an X-ray non-filtering position, and being positioned between the X-ray source and the X-ray detector; and
   a controller programmed to acquire a first set of projection data when applying a first energy spectrum by controlling the X-ray source to emit the X-rays with the first energy spectrum and controlling one or more of the micro-filters to be in the non-filtering position, and to further acquire a second set of projection data when applying a second energy spectrum with a mean energy greater than the mean energy of the first energy spectrum by controlling the X-ray source to emit the X-rays at the second energy spectrum and controlling one or more of the micro-filters to be in the filtering position.

2. The multi-energy X-ray imaging system of claim 1, wherein the controller is programmed to transition one or more of the micro-filters between the X-ray filtering position and the X-ray non-filtering position in less than approximately 10 microseconds.

3. The multi-energy X-ray imaging system of claim 1, wherein when one or more of the micro-filters are in the non-filtering position, greater than 75% of the emitted X-rays pass through the filtering device.

4. The multi-energy X-ray imaging system of claim 1, comprising a processor configured to process the first set of projection data and the second set of projection data to construct one or more multi-energy X-ray images.

5. The multi-energy X-ray imaging system of claim 1, wherein the controller is programmed to transition the one or more micro-filters between the filtering position and the non-filtering position via one of electrostatic, thermal, or magnetic actuation.

6. An X-ray imaging system, comprising:
   an X-ray source configured to emit X-rays toward an imaging volume;
   an X-ray detector configured to produce an electrical signal corresponding to the intensity of the X-rays that reach the X-ray detector after traveling through the imaging volume;
   a filtering device positioned between the X-ray source and the X-ray detector, the filtering device comprising one or more micro-filters each configured to transition between an X-ray filtering position and an X-ray non-filtering position; and
   a controller programmed to acquire a set of projection data when controlling the one or more micro-filters to be in either a non-filtering position or a non-filtering position so as to modulate one or more of the X-ray flux or spectral characteristics within the imaging volume or at the detector.

7. The X-ray imaging system of claim 6, wherein the one or more of the micro-filters, when in the filtering position, block portions of the X-rays beam outside one or more regions of interest in the object.

8. The X-ray imaging system of claim 6, wherein the controller is further programmed to individually control one or more of the micro-filters to one or more of modify the spectral characteristics of the X-ray beam incident on the imaging volume and vary the attenuation within a field of view to provide a uniform flux profile at the X-ray detector during acquisition of the projection data.

9. The X-ray imaging system of claim 6, wherein the controller is further programmed to individually control one or more of the micro-filters to block a portion of the effective area of a plurality of detector cells of the X-ray detector during acquisition of the projection data.

10. A multi-energy X-ray imaging method, comprising:
controlling an X-ray source to emit X-rays with a first energy spectrum;
controlling one or more of micro-filters, positioned between the X-ray source and an X-ray detector, to be in an X-ray non-filtering position when the X-ray source emits the X-rays with the first energy spectrum;
controlling the X-ray source to emit the X-rays with a second energy spectrum with a mean energy greater than the mean energy of the first energy spectrum; and
controlling the one or more micro-filters to be in an X-ray filtering position when the X-ray source emits the X-rays with the second energy spectrum.

11. The multi-energy X-ray imaging method of claim 10, comprising acquiring a first set of projection data when applying the first energy spectrum by detecting X-rays that pass between the array of micro-filters and through an imaging volume, and acquiring a second set of projection data when applying the second energy spectrum by detecting X-rays that traverse the array of micro-filters and through the imaging volume.

12. The multi-energy X-ray imaging method of claim 11, comprising constructing one or more multi-energy X-ray images from the first set of projection data and the second set of projection data.

13. The multi-energy X-ray imaging method of claim 10, wherein controlling the array of micro-filters to be in the X-ray filtering position or to be in the X-ray non-filtering position comprises altering the physical position of micro-filters in the array.

14. The multi-energy X-ray imaging method of claim 13, wherein altering the physical position of micro-filters in the array comprises pivoting each of the miocro-filters in the array of micro-filters on a respective torsion spring.

15. The multi-energy X-ray imaging method of claim 13, wherein altering the physical position of the micro-filters in the array comprises applying one of a voltage, a magnetic field, or a thermal field to the micro-filters in the array to alter the configuration of the micro-filters in the array to the X-ray filtering position or the X-ray non-filtering position.

16. An X-ray imaging method, comprising:
controlling an X-ray source to emit X-rays;
controlling one or more of micro-filters, positioned between the X-ray source and an X-ray detector, each configured to transition between an X-ray filtering position and an X-ray non-filtering position, so as to modulate one or more of the X-ray flux or spectral characteristics within the imaging volume or at the detector; and
controlling acquisition of projection data by the X-ray detector when the one or more micro-filters are configured in either the X-ray filtering position or the X-ray non-filtering position.

17. The X-ray imaging method of claim 16, wherein the one or more of the micro-filters when in the filtering position, block portions of the X-rays beam outside one or more regions of interest in the object.

18. The X-ray imaging method of claim 16, wherein one or more of the micro-filters are individually controlled to vary the attenuation within a field of view, thereby achieving one or more of modifying the spectral characteristics of the X-ray beam incident on the imaging volume and providing a uniform flux profile at the X-ray detector during acquisition of the projection data.

19. The X-ray imaging method of claim 16, wherein the one or more of the micro-filters are individually controlled to block a portion of the effective area of a plurality of detector cells comprising the X-ray detector during acquisition of the projection data.

20. The X-ray imaging method of claim 16, wherein controlling the one or more micro-filters to transition between the X-ray filtering position and the X-ray non-filtering position comprises, individually or in subsets, pivoting micro-filters on respective torsion springs or applying one of a voltage, a magnetic field, or a thermal field to the micro-filters to alter the configuration of the micro-filters.

* * * * *